(12) United States Patent
Sendijarevic et al.

(10) Patent No.: US 7,276,036 B2
(45) Date of Patent: *Oct. 2, 2007

(54) FOAM ARTICLES

(75) Inventors: Vahid Sendijarevic, Troy, MI (US);
Aisa Sendijarevic, Troy, MI (US);
Ibrahim Sendijarevic, Troy, MI (US)

(73) Assignee: Troy Polymers, Inc., Troy, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/242,373

(22) Filed: Oct. 3, 2005

(65) Prior Publication Data

US 2006/0029790 A1    Feb. 9, 2006

Related U.S. Application Data

(63) Continuation of application No. 10/841,298, filed on May 7, 2004, now Pat. No. 6,984,216.

(60) Provisional application No. 60/469,609, filed on May 9, 2003.

(51) Int. Cl.
*A61F 5/00*    (2006.01)

(52) U.S. Cl. .............................. 602/8; 602/6

(58) Field of Classification Search .................... 602/5, 602/6, 8
See application file for complete search history.

(56) References Cited

U.S. PATENT DOCUMENTS

| 3,874,376 | A |  | 4/1975 | Dart et al. |
|---|---|---|---|---|
| 3,972,323 | A |  | 8/1976 | Boricheski |
| 4,131,114 | A |  | 12/1978 | Kirkpatrick et al. |
| 4,351,683 | A |  | 9/1982 | Kusilek |
| 4,376,438 | A |  | 3/1983 | Straube et al. |
| 4,433,680 | A |  | 2/1984 | Yoon |
| 4,502,479 | A |  | 3/1985 | Garwood et al. |
| 4,609,578 | A |  | 9/1986 | Reed |
| 4,655,208 | A |  | 4/1987 | Yoon |
| 4,667,661 | A |  | 5/1987 | Scholz et al. |
| 4,683,877 | A |  | 8/1987 | Ersfeld |
| 4,688,563 | A |  | 8/1987 | Hanssen |
| 4,841,958 | A |  | 6/1989 | Ersfeld et al. |
| 4,888,225 | A |  | 12/1989 | Sandvig et al. |
| 4,946,726 | A |  | 8/1990 | Sandvig et al. |
| 5,014,403 | A |  | 5/1991 | Buese |
| 5,244,997 | A |  | 9/1993 | Scholz et al. |
| 5,718,674 | A |  | 2/1998 | Penrose et al. |
| 6,103,152 | A | * | 8/2000 | Gehlsen et al. ............ 264/45.4 |
| 6,537,934 | B1 | * | 3/2003 | Yeo .......................... 442/149 |
| 6,984,216 | B2 | * | 1/2006 | Sendijarevic et al. .......... 602/8 |
| 2004/0002671 | A1 | * | 1/2004 | Reaux ............................ 602/5 |

FOREIGN PATENT DOCUMENTS

GB    1533989    11/1978
JP    7212235 A   12/1982

OTHER PUBLICATIONS

Faso and stills, "Journal of Prosthetics and Orthotics," 1991 3(2) 55-58.

* cited by examiner

*Primary Examiner*—Kim M. Lewis
(74) *Attorney, Agent, or Firm*—Brooks Kushman P.C.

(57) ABSTRACT

An article including a polymeric foam having a thickness of less than about 3/16 inch (about 5 mm) and one or more curable resins.

20 Claims, 7 Drawing Sheets

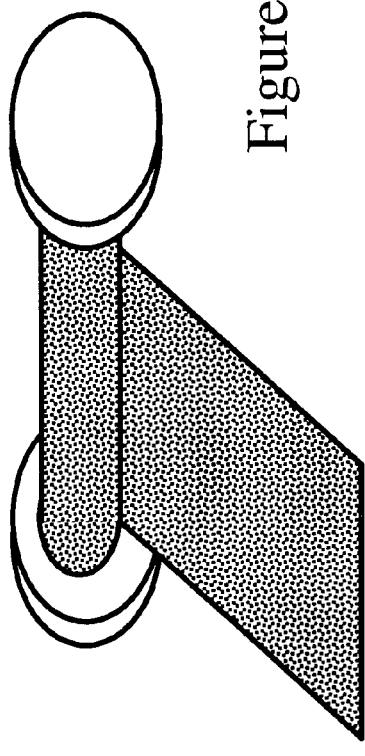
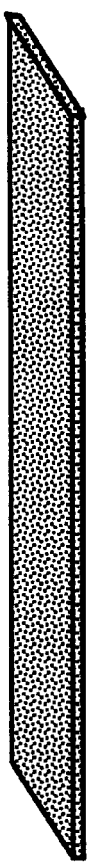
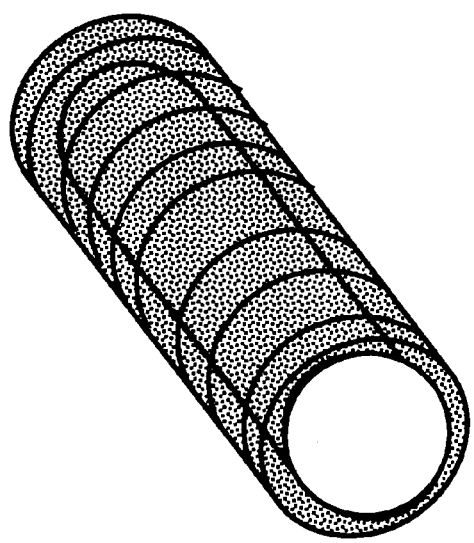
Figure 5a
Figure 5b
Figure 5c

FOAM ARTICLES

CROSS-REFERENCE TO RELATED APPLICATIONS

This application is a continuation of and claims priority to U.S. application Ser. No. 10/841,298, filed May 7, 2004, issued on Jan. 10, 2006 as U.S. Pat. No. 6,984,216, which claims the benefit of U.S. provisional application Ser. No. 60/469,609, filed on May 9, 2003.

BACKGROUND OF THE INVENTION

1. Field of the Invention

One aspect of the present invention is a polymeric foam containing one or more curable resins.

2. Background Art

There are various types of immobilization tapes and splints available on the market and described in literature. Plaster of Paris casting tapes, used since the $19^{th}$ century, Faso and Stills, *JOURNAL OF PROSTHETICS AND ORTHOTICS,* 1991, 3(2), 55-58, are basically gauzes impregnated with gypsum. They are activated by immersion in water for a few seconds and then applied around joints or fractures before they set hard. The set time for Plaster of Paris tapes can be long before their maximum strength is achieved. The main disadvantages of Plaster of Paris immobilization tapes are their poor strength to weight ratios, which results in finished casts and splints that are often bulky and heavy, and poor resistance to water, which makes showering and bathing difficult.

More recently, synthetic casting and immobilization tapes and splits were developed, which consist of substrates and water curable polymeric resins. The polymeric resins can be water cured or water reactive NCO-polyurethane prepolymers, as disclosed in U.S. Pat. Nos. 4,131,114; 4,376,438; 4,433,680; 4,502,479; 4,655,208; 4,667,661; and 5,244,997. The water cured polymeric resins can be coated onto substrates which are most commonly fiberglass or polyester, as disclosed in U.S. Pat. Nos. 3,972,323; 4,502,479; 4,688,563; 4,609,578; 4,841,958; and 5,014,403. There are numerous polyisocyanate immobilization tapes available on the market. The set time of synthetic tapes is, in general, shorter than that for Plaster of Paris tapes. The synthetic casts have good resistance to water and higher strength-to-weight ratio than Plaster of Paris tapes.

Woven or knitted fiberglass fabrics are frequently utilized as substrates to carry the water curable resins, as disclosed in U.S. Pat. Nos. 4,502,479; 4,668,563; 4,609,578; and 5,014,403. The fiberglass fabric is commonly cut before application, which can results in fibers sticking out. After the water curable prepolymer resin cures and tapes harden, the fibers can protrude from the edges and can become needle-like and can penetrate the protective fabric and contact the skin resulting in cuts and skin irritation. Similar problems can occur with substrates fabricated from other woven or knitted fibers. In addition, during the cutting of cured tapes, the fiberglass particles can become air-born, which can be hazardous if inhaled. In addition, water curable polymeric resins may have insufficient adhesion to the fiberglass.

Woven or knitted polyester fibers are also widely used as substrates that carry water curable polymeric resins. Polyester tapes are softer and have better elasticity than fiberglass tapes. However, polyester substrates can be susceptible to moisture, which can affect the stability of the water curable polymeric resins and therefore shelf-stability of the tapes or splints.

Other types of immobilization tapes have been developed that utilize woven and non-woven substrates that include natural organic fabrics (e.g. cotton and wool), natural organic polymers fibers (e.g. acetate, rayon), synthetic organic polymers fibers (nylon), etc. The non-woven substrates tend to have smoother edges than woven substrates, however, they tend to be thicker, which makes it more difficult to evenly spread the water curable resins, and can lessen the moldability of tapes and splints as disclosed in U.S. Pat. Nos. 4,351,683; 4,683,877; 4,888,225; and 4,946,726.

U.S. Pat. Nos. 4,888,225 and 4,946,726 disclose orthopedic splinting articles for use with animal body parts, which comprise of a cellular material unitary blank with water curable isocyanate functional polyurethane prepolymer resin. The blank is dimensioned to extend the length of the body part to be immobilized and to partially, but not completely, extend around the circumference of the body part. These splinting articles are limited to pre-fabricated designs, manufactured from one piece and one layer of cellular material unitary blank which is one-quarter inch to one-half inch thick. It is extremely difficult to evenly load viscous curable isocyanate resins throughout such thick cellular foams blank, which can lead to suboptimal properties of cured orthopedic splinting articles.

As an alternative, U.S. Pat. Nos. 4,888,225 and 4,946,726 propose that a water-curable resin can be prepared by reacting polyol and polyisocyanate reagents in-situ in the foam substrate, which can be very difficult to control as the reagents would not necessarily get adequate mixing, which could lead to incomplete reaction and in turn to poor quality water-curable resin in the foam substrate. Furthermore, side reactions with foam substrate can occur which can further change the properties of the curable resin and the foam substrate. As a result, these splinting articles based on a one layer, unitary blank have found limited, if any, application in the orthopedic splinting applications.

U.S. Pat. No. 3,728,206 discloses a composite orthopedic supportive structure comprised of a non-woven open cell foam that is impregnated with crystalline thermoplastic material such as polyisoprene. This orthopedic supportive structure is heated to an elevated temperature until the crystalline thermoplastic material melts and it is applied to the body part while hot. The composite subsequently crystallizes and hardens when cooled down to room temperature. Additionally, the cooling of the crystalline thermoplastic material can take a relatively long time, which is undesirable in immobilization applications. Furthermore, application to the body member while hot makes the utilization of such orthopedic supportive structures extremely undesirable as it may result in burns. Therefore, these orthopedic supportive structures have found no significant, if any, application in the orthopedic immobilization applications.

In light of the foregoing, there is a need for the orthopedic immobilization tapes which are not woven and not knitted, that can be soft and flexible, can have good moldability, can have good adhesion to curable resin and that can facilitate easy loading of the resin into the substrate, and the orthopedic immobilization tapes thin enough that can be used as orthopedic winding casting tapes or layered for use in orthopedic casting splinting articles, that when cured can harden adequately to provide required immobilization.

SUMMARY OF THE INVENTION

According to one embodiment of the present invention, an orthopedic casting article including a polymeric foam tape containing one or more curable resins is disclosed. The one or more curable resins can applied on one side or both sides of the polymeric foam tape. In certain applications, the polymeric foam tape can have a thickness of about 1/128 inch (about 0.2 mm) to about 3/16 inch (about 5 mm), a width of about 1/2 inch to about 24 inches, and a length of at least about 6 inches. The polymeric foam can be thermosetting or thermoplastic, and can have a uniform or variable polymer composition structure. The polymeric foam can be flexible, semi-rigid, semi-flexible, viscoelastic, resilient or rigid. The polymeric foam can have a substantially open cell structure, a substantially closed cell structure, or a substantially reticulated cell structure. In certain applications, the polymeric foam can have an average cell density greater than about 10 pores per inch (ppi) and an elasticity greater than about 1%. The polymeric foam can be a foam having an affinity to water in the range of hydrophilic to hydrophobic. The average density of the polymeric foam used in certain applications of the present invention can be about 1.6 kg/m$^3$ to about 960 kg/m$^3$.

The polymeric foam tape can include a foam having at least one variable property throughout, wherein the variable property is selected from the group consisting of density, cell density, cell geometry, cell size, affinity to water, elasticity, thickness and width. The polymeric foam tape can include a foam based on one or more isocyanate or isocyanate containing compounds. The one or more isocyanates and isocyanate containing compounds can include aliphatic isocyanate, aromatic isocyanate, cycloaliphatic isocyanate or a mixture thereof. In certain applications, the polymeric foam tape includes a polyurethane foam, being a product of a reaction of one or more polyols with one or more isocyanates or isocyanate containing compounds. In other applications, the polymeric foam tape includes a polyurea foam, being a product of a reaction of one or more polyamines with one or more isocyanates or isocyanate containing compounds. As non-limiting examples, The polymeric foam tape can be selected from the group consisting of polyolefin-based polymers, polyester-based polymers, polyether-based polymers, polystyrene-based polymers, and mixtures thereof.

The polymeric foam tape can include one or more additives to alter the surface properties of the polymeric foam or adhesion to the one or more curable resins. The curable resin can be applied to the polymeric foam tape at a load of about 99/1 resin to polymeric foam tape weight ratio to 1/99 resin to polymeric foam tape weight ratio. In certain applications, at least one of the one or more curable resins can be a water-curable resin. In other applications, at least one of the one or more water curable resins can be an isocyanate containing material. The isocyanate containing material can be selected from the following group: aromatic isocyanates, aliphatic isocyanates, cycloaliphatic isocyanates, isocyanate-based adducts, isocyanate-based derivatives, isocyanate-prepolymers, isocyanate-oligomers and isocyanate-quasi prepolymers. In certain applications, the isocyanate containing material has an isocyanate to active hydrogen equivalent weight ratio greater than about 1. The isocyanate containing material can contain at least one catalyst promoting the reaction of the isocyanate with water. In certain applications, at least one of the one or more water curable resins can be Plaster of Paris. At least one of the one or more curable resins can be cured via chemical reaction, UV light, laser light, radiation, or heat induced reaction.

According to another embodiment of the present invention, an orthopedic casting splint including two or more layers is disclosed. One or more of the layers includes a polymeric foam tape containing one or more curable resins. The polymeric foam tape can include a thermoset or thermoplastic polymeric foam. The polymeric foam tape can include a foam having a substantially open cell structure, a substantially closed cell structure, or a substantially reticulated cell structure. One or more layers of the splint can include a woven, non-woven, knitted, or extruded layer. In certain applications, the splint can be made in the shape of a sleeve or glove.

In yet another embodiment, a method for applying an orthopedic casting article to a body member is disclosed. The method includes winding a polymeric foam tape containing one or more curable resins around a body member; and curing the one or more curable resins before, during, or after the polymeric foam tape is wound around the body member. In certain applications, the method can further include cutting or slicing the polymeric foam tape to a length capable of partially or fully immobilizing the body member.

In another embodiment of the present invention, a method for applying an orthopedic casting splint to a body member is disclosed. The method includes providing a splint comprising two or more layers of a polymeric foam tape, wherein at least one of the layers contains one or more curable resins; fully or partially enveloping the splint around a body member; and curing the one or more curable resins before, during, or after the polymeric foam tape is enveloped around the body member. In certain applications, the method can further include cutting or slicing the splint to a shape capable of partially or fully immobilizing the body member. The enveloping step can include inserting the body member into the splint.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings which:

FIG. 5a depicts a role of continuous single-layered foam tape containing a curable resin in accordance with one embodiment of the present invention;

FIG. 5b depicts the role of FIG. 5a which has been cut into a desired length;

FIG. 5c depicts the desired length of 5b which has been wound around a body member;

DETAILED DESCRIPTION OF EMBODIMENTS OF THE PRESENT INVENTION

Figure 1B:
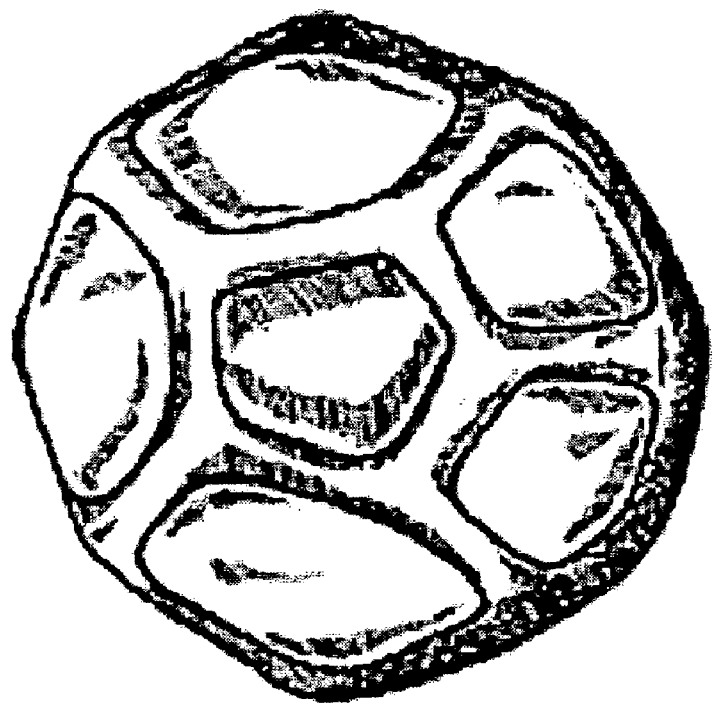
FIGS. 1a and 1b depict schematics of cell structural elements in foams with open and closed cells, respectively.
Figure 1A:
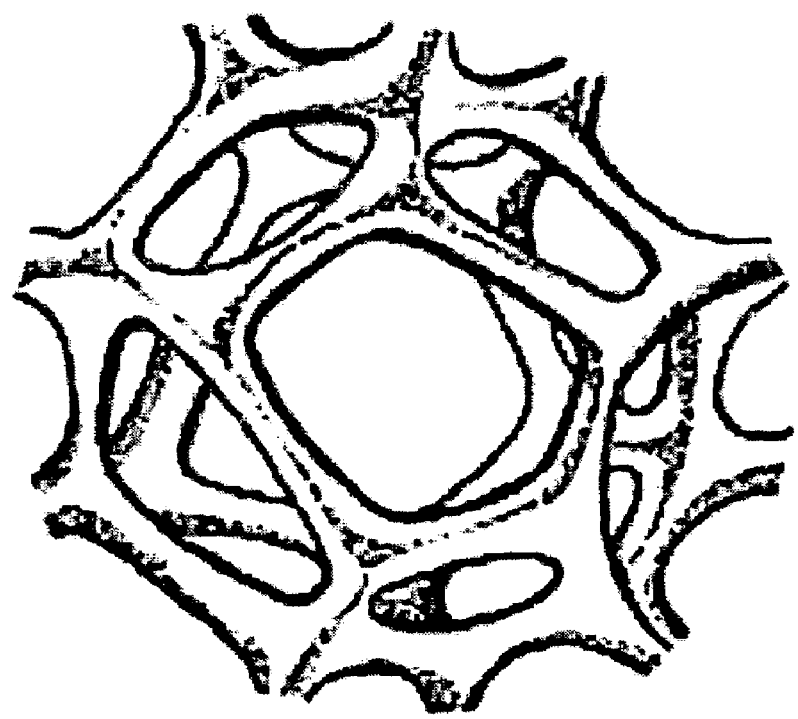
Figure 2:
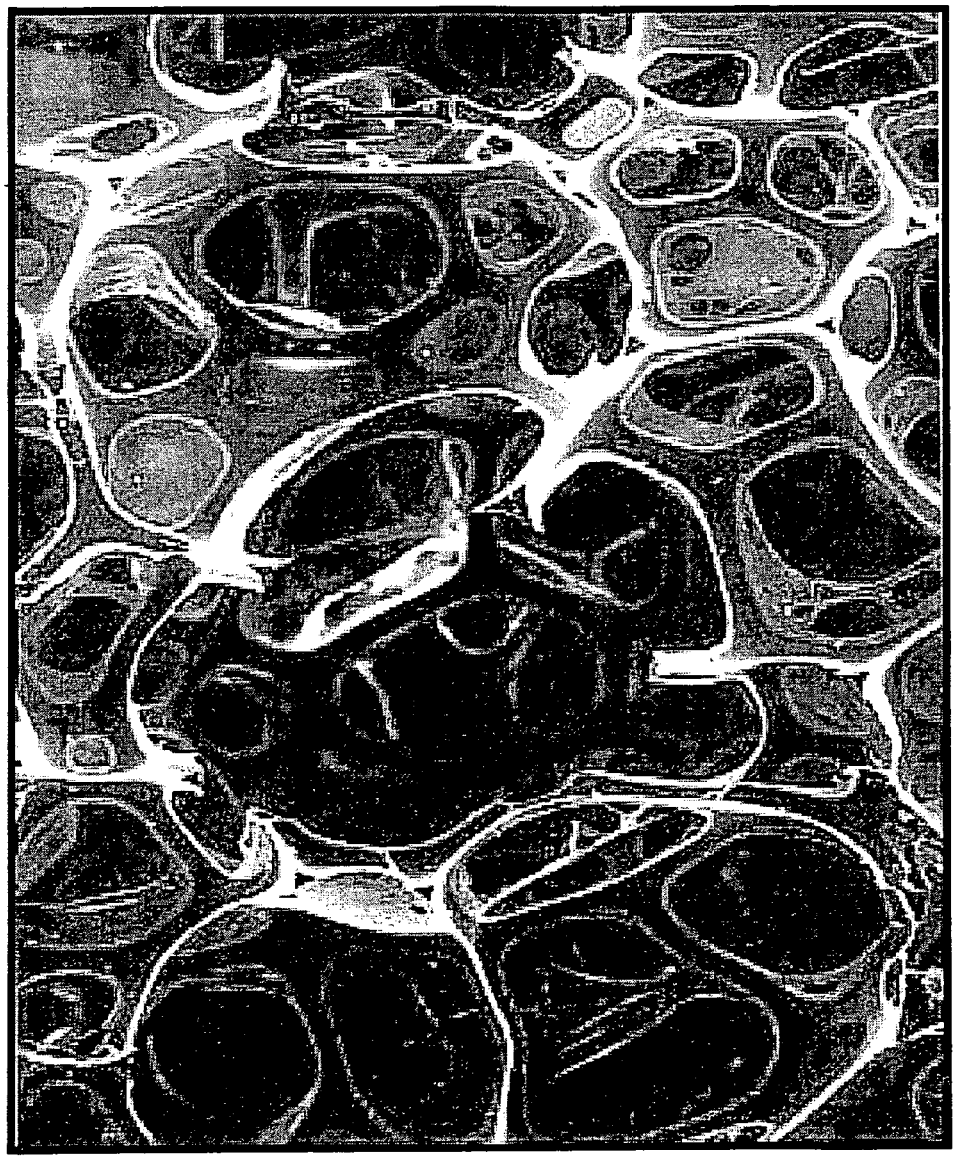
FIG. 2 depicts a microscopic image of foam with open cell structure.
Figure 3:
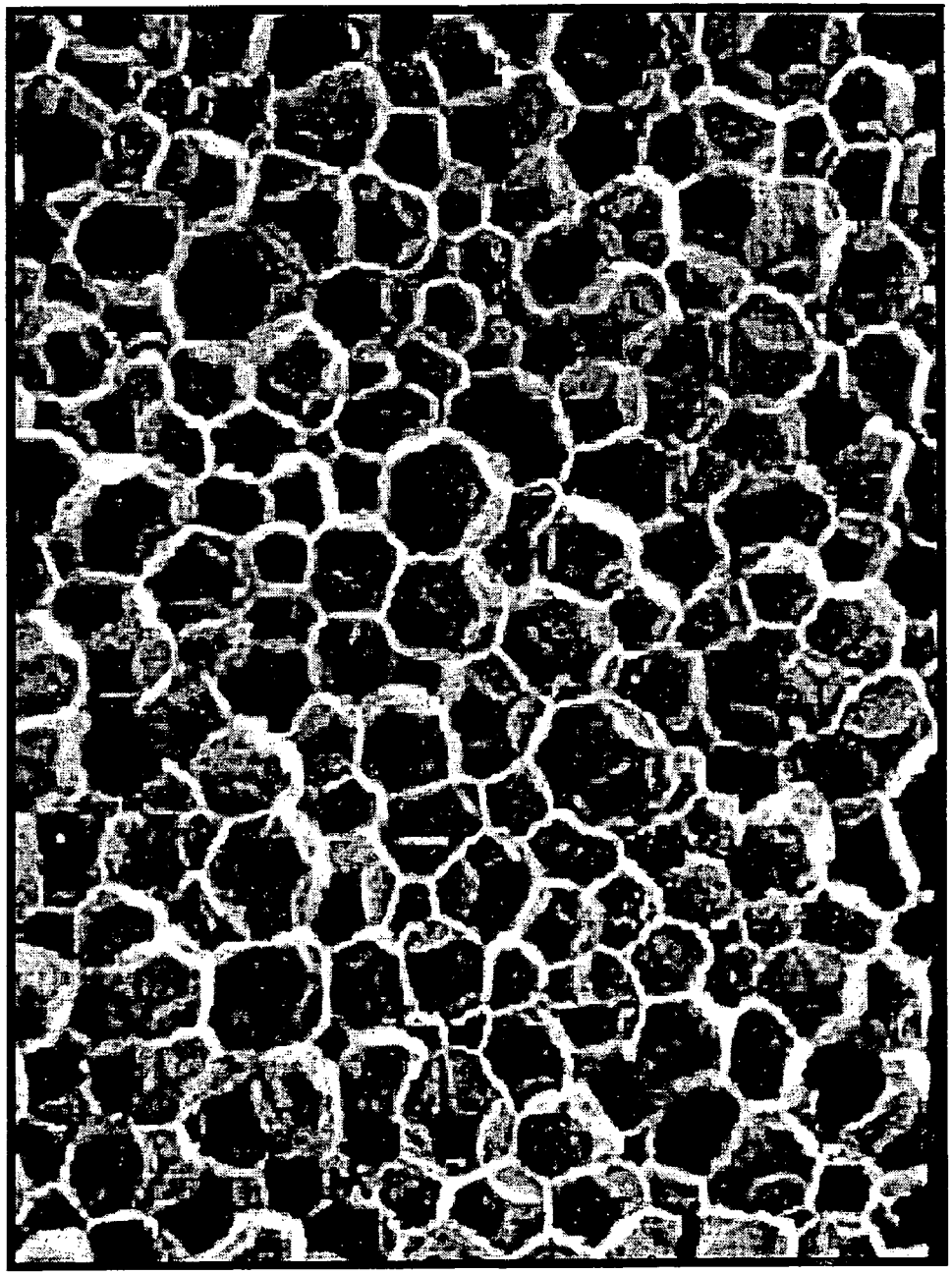
FIG. 3 depicts a microscopic image of a foam with a mixture of closed and open cells.

As required, detailed embodiments of the present invention are disclosed herein. However, it is to be understood that the disclosed embodiments are merely exemplary of an invention that may be embodied in various and alternative forms. Therefore, specific functional details disclosed herein are not to be interpreted as limiting, but merely as a representative basis for the claims and/or as a representative basis for teaching one skilled in the art to variously employ the present invention.

One aspect of the present invention provides orthopedic immobilization tapes and casting articles that for at least one of its components contain a polymeric foam tape substrate onto which a curable resin is applied. A variety of polymeric foams can be used in the present invention that includes polyurethane foams. Other non-limiting examples of polymeric foams that can be used in accordance with the present invention include polyurea foams, polyolefin foams, polyester foams, polystyrene foams, and polyether foams. A variety of curable resins can be used that include water-curable resins, and water-curable polyurethane resins.

One aspect of the present invention provides orthopedic immobilization tapes and casting articles that for at least one of its components contain a polymeric foam tape substrate onto which a curable resin is applied.

A variety of polymeric foams can be used in the present invention that includes polyurethane foams. The cell structure of the polymeric foams can be closed or open, preferably mostly open, and most preferably fully open and/or reticulated open cell structure. Depending on the application needs of the immobilization tape or casting article, the polymeric foams can be rigid, semi-flexible, or flexible. The foams can have elasticity greater than about 1%. A variety of additives can be added to the foam to affect their physical properties, mechanical properties, surface properties, color, tackiness, adhesion to resins, etc.

A variety of curable resins can be used that, as non-limiting examples, include water-curable resins and water-curable polyurethane resins. A variety of additives can be added to the curable resins to affect their adhesion to the foam, color, tackiness of the tape, cured physical and mechanical properties of the tape, surface properties of the tape before and/or after curing, etc.

Curable resins can be coated or applied onto polymer foam tape substrates according to any techniques utilized in coating or application of curable resins onto substrates (woven, non-woven, knitted, extruded, etc.) including, but not limited to, roller coating, spray coating, transfer coating, immersion coating, or any other method known to those in the art of coatings and coating application.

The orthopedic immobilization tapes and casting articles of the present invention are packaged in a way to minimize exposure to water that includes, but is not limited to, dry packaging, vacuum packaging, etc.

The orthopedic immobilization tapes and casting articles, that include splints, are used in a manner which is typical for synthetic orthopedic tapes and casting articles.

Synthetic orthopedic tapes and casting articles, including splints, are disclosed that for at least one of its components contain a polymeric foam tape substrate onto which a curable resin is applied. Various types of polymeric foam materials can be utilized in the present invention that include polyurethane foams, and foams with a variety of cell structures, in particular foams with mostly open, and fully open cell structures that include reticulated foams. In certain embodiments, thin substantially open cell and reticulated foams with thickness dimensions of less than about $3/16$ inch allow for a substantially even distribution of the resin through the foam thickness, resulting in cured tapes with good immobilization properties. Furthermore, for thin tapes with thickness dimension of less than about 2 mm, in addition to substantially open cell foams, partially closed or substantially closed cell foams can satisfactorily absorb the curable resin. Various types of curable resins can be applied on the polymeric foam tape substrates. In some embodiments, these resins are water curable resins, and in other embodiments they are water curable polyurethane-based resins.

One aspect of this invention relates to orthopedic immobilization tapes and casting articles, including splints, having at least one layer of foam tape which contains one or more curable resins. In particular, at least one of the substrates, onto which curable resins are applied, is made of polymeric cellular tape materials or polymeric foam tape.

The polymeric foams (or polymeric cellular materials) can be prepared virtually from any polymer by the introduction of gas into polymer matrix, as is known to those familiar in the art of polymeric foam synthesis and preparation. Polymeric foams used in the present invention can have density from about 1.6 kg/m³ to about 960 kg/m³ (about 0.1 pcf to about 60 pcf) and can have uniform or variable density throughout its thickness.

The foaming of polymeric foams can be carried out by chemical, physical or mechanical means (Handbook of Polymeric Foams and Foam Technology, Hanser Publishers. 1991/edited by D. Klempner & K. C. Frisch). A non-limiting examples of foaming techniques includes:

a. Volatilization of low-boiling liquids (such as fluorocarbons or methylene chloride) within the polymer mass as a result of the exothermic heat of reaction or by application of heat.
b. Volatilization of gasses produced during polymerization, such as in the reaction of isocyanate and water in the polyurethane foam formation.
c. Thermal decomposition of chemical blowing agents, which generate gases through application of heat or exothermic heat of polymerization reaction.
d. Mechanical whipping of gases (frothing) into polymer system (melt, solution or suspension), which hardens either by catalytic action and/or heat, entrapping the gas bubbles in the matrix.
e. Expansion of gas dissolved in a polymer mass upon reduction of the pressure in the system.
f. Incorporation of hollow microspheres into polymer mass.
g. In addition to the above listed techniques, foams can be used in the tape substrates of the presented invention prepared according to any method known to those skilled in the art of polymeric foam synthesis and preparation.

Figure 6A:
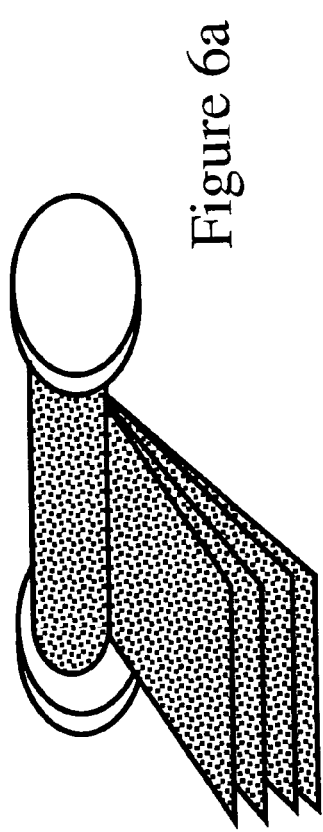
FIG. 6a depicts a role of continuous multi-layered foam tape in which at least one layer of foam tape containing a curable resin in accordance with one embodiment of the present invention.
Figure 6B:
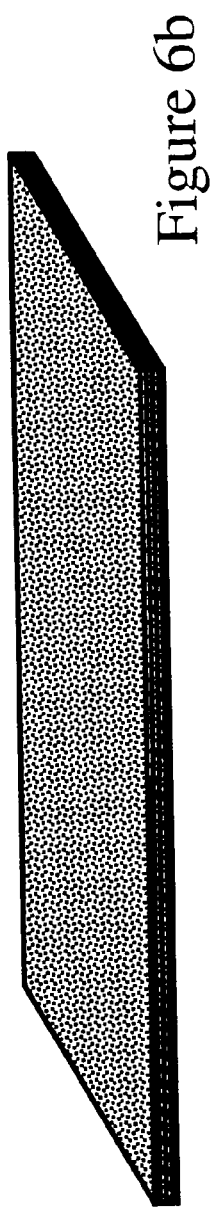
FIG. 6b depicts the role of FIG. 6a which has been cut into a desired length.
Figure 6C:
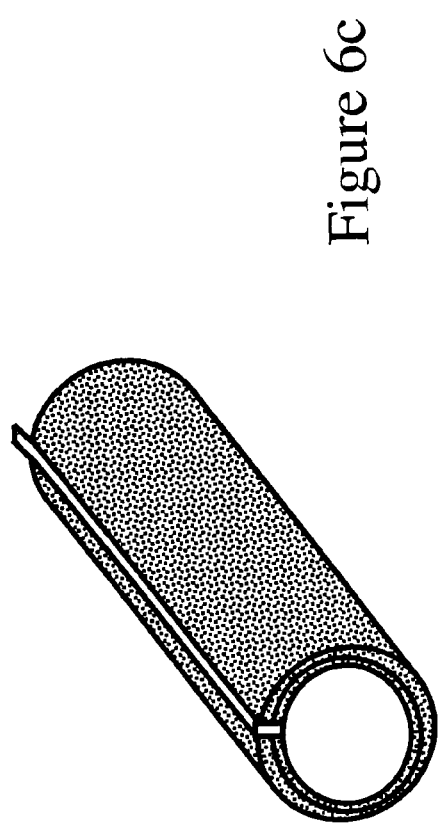
FIG. 6c depicts the desired length of FIG. 6b which has been enveloped around a body member as a splint to partially or completely immobilize a circumference of the body member.
Figure 7:
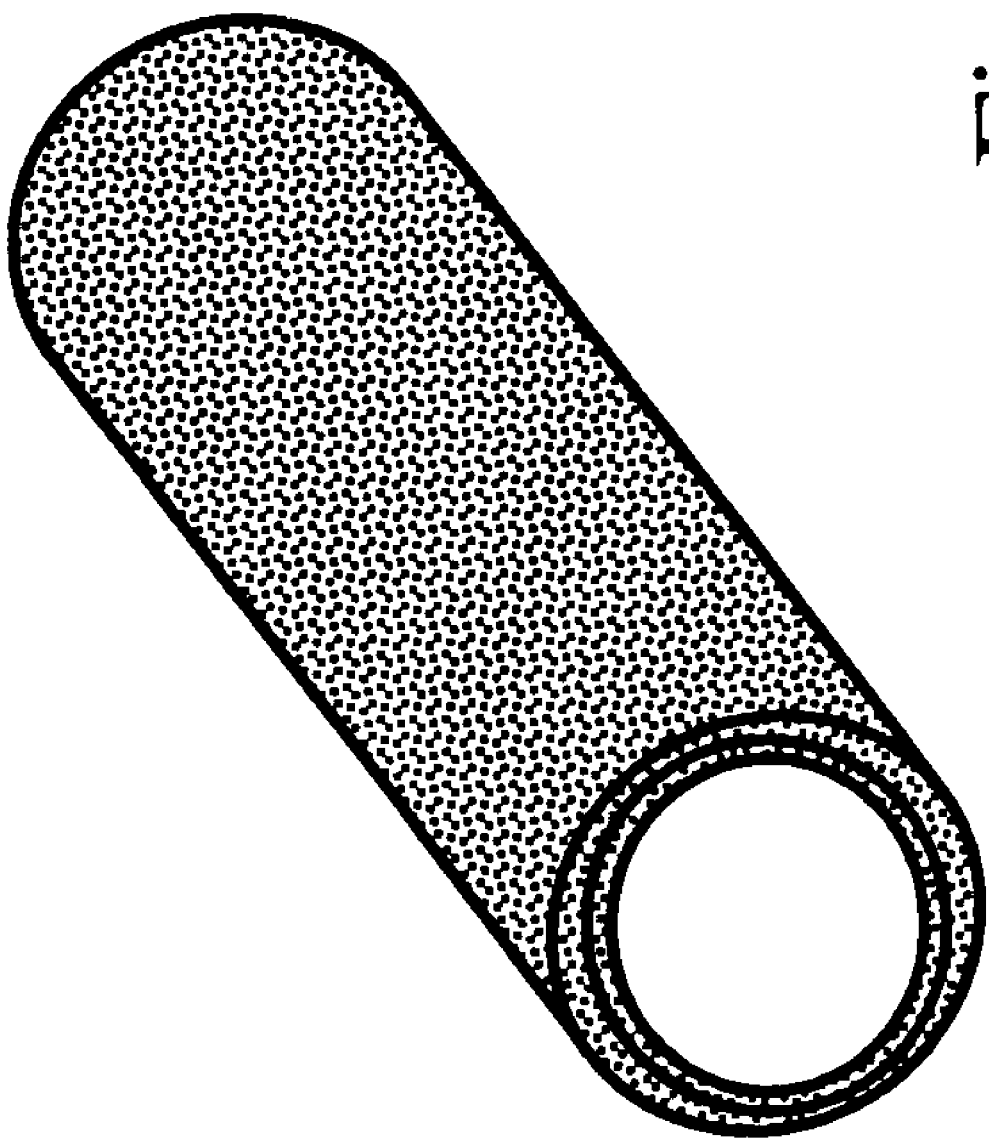
FIG. 7 depicts a multi-layered foam sleeve tube which contains a curable resin that is pulled onto a body member as to partially or completely immobilize a circumference of the body member.

The polymeric foams can be thermoplastic or thermosetting. The polymeric foams can be made of a variety of chemical compositions and chemical blends. In addition, blends and composites of two or more polymeric foams can be used as the foam tape substrates of the present invention, that can have same or different chemical compositions, molecular weights, cell size and morphology (geometry, weight distribution between windows and struts), and bulk densities. The foam tape substrates can, but do not necessarily have to, contain one or more organic and/or inorganic fillers and additives, which as non-limiting examples can include glass beads, ceramics, organic fibers, carbon black, dyes, lubricants, tack control agents, fiberglass, etc. Composites of polymeric foams with fiberglass, polyester, natural fiber, synthetic fibers, and non-cellular polymeric materials and substrates can be utilized in the orthopedic tapes (see FIGS. 5a, 5b, and 5c) and casting articles (including splints) of this invention as well. According to FIGS. 6a, 6b, and 6c, a casting splint can be multi-layered with at least one layer comprised of a foam tape substrate that contains a curable resin.

The polymeric foams used in the present invention can have cells with a variety of cell shapes, cell sizes, and morphologies. The foams can have uniform or varying cell size, cell shapes, and cell density throughout its thickness. In the polymeric foam tape substrates used in the present invention, the foam cell structure may be open (tunnels between cells) or closed cells (windows separating cells), or any mixture of open/closed cells, or reticulated open cell structure. In certain embodiments, the substrates are made of polymeric tape foam that have mostly open cells structure, fully open cells structure, and more specifically in certain embodiments an open reticulated structure. Foams with closed or mostly closed cell structure can be used if adequate number of cells are opened during any point of the fabrication process (non limiting example is crushing). The cell density in the polymeric foam substrates can vary from about 3 cells (pores) per inch (ppi) to about 1000 ppi.

Figure 4:
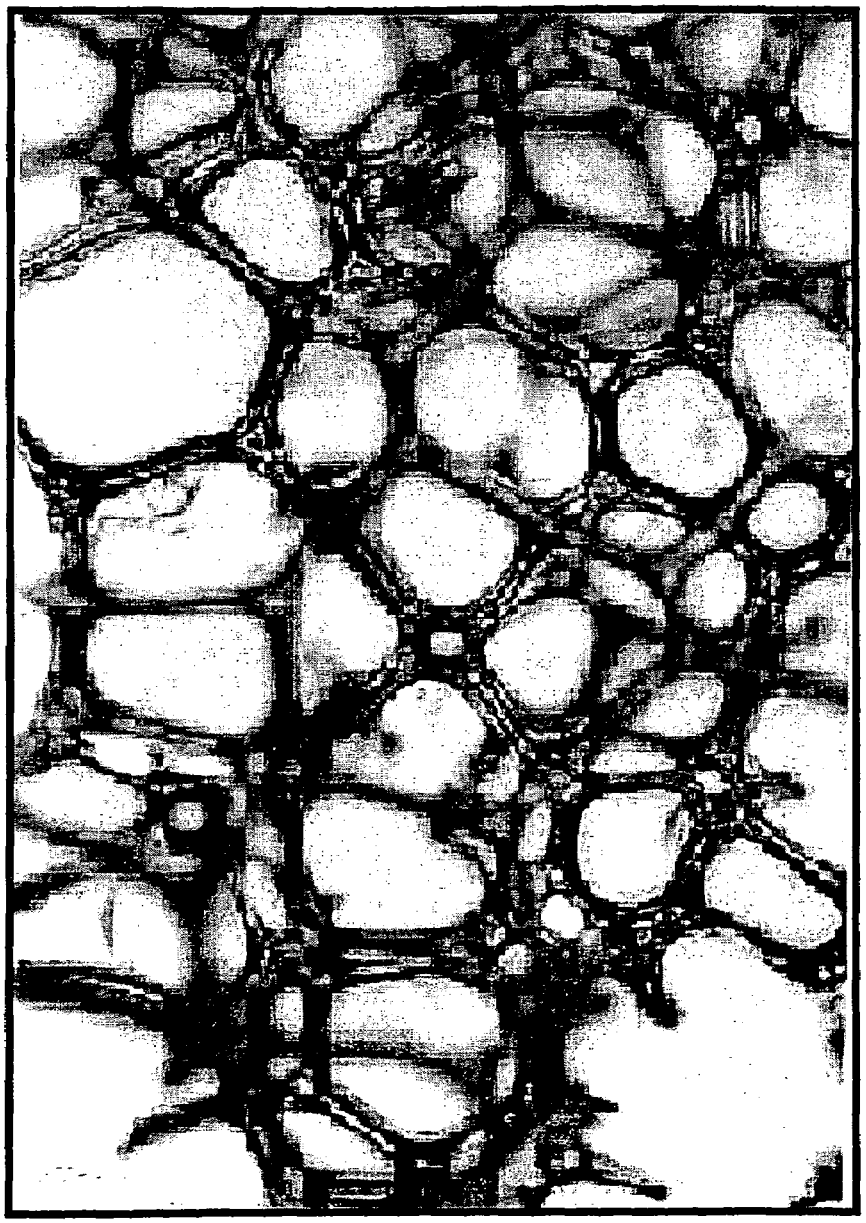
FIG. 4 depicts a microscopic image of a foam with an open reticulated cell structure.

Reticulated foams are a special type of open cell structure foams in which the cells do not have windows, but only the cell struts. (HANDBOOK OF POLYMERIC FOAMS AND FOAM TECHNOLOGY, Hanser Publishers 1991/edited by D. Klempner & K. C. Frisch.) Reticulated foams are typically prepared by removal of the cell windows in the post-treatment procedure of the already made foam, either by melting (thermal procedure) or by dissolving (solvents, alkaline solutions). Reticulated foams prepared by any method or procedure can be used as the foam tape substrates in the present invention. As a non-limiting example, an image of a polyurethane reticulated foam is shown in FIG. 4. General information on commercial reticulated polyurethane foam products, as non limiting examples, can be found in the Technical Product Function Sheet, Foamex Co., 1500 East Second Street, Eddistone, Pa. 19022.

Polymeric foam tape substrates used in the present invention can be produced of various shapes, lengths, thicknesses, or widths. These tape substrates can be made by a variety of methods that are known to those familiar with the art of polymer manufacturing. As a non-limiting example, a continuous sheet of polymeric foam tape substrate (see FIGS. 5a, 5b, and 5c and FIGS. 6a, 6b, and 6c) can be sliced or cut from a cylindrical shaped polymeric foam bun. After slicing or cutting the polymeric foam tape substrate can be, but does not necessarily have to be, thermoformed entirely or partially to reinforce the tapes, change density, alter porosity, or introduce a variety of patterns, including alternating thick and thin parts. If needed the foams can be also sewn, stapled, and/or glued. A stretchable sleeve can be cut from a cylindrical shaped polymeric foam bun onto which a water curable resin is applied, and that could be used as a splint or immobilization orthopedic tape. A stretchable sleeve can be made by a variety of methods that, as non-limiting examples, include gluing, stapling, sewing, melting, and/or pressing together opposite edges of a sheet.

Polymeric foams used in the present invention can have a range of flexibilities that include flexible, semi-rigid, and rigid foams. In some embodiments, semi-rigid foam is used, and in other embodiments, flexible foams are used.

In one embodiment, it is preferred, that polymeric foams, including polyurethane foams, are viscoelastic (energy absorbing) and flexible foams that have good moldability that allows the casting tapes and casting article to effectively align to the morphology of the body.

In another embodiment, high resilient polymeric foam tape substrates can be used in the casting tapes and casting articles of the present invention.

The elasticity of the foam tape substrates can be about 1% or higher. As non-limiting examples, the elasticity of foams can be controlled by the chemical composition of the foams, cell structures, bulk density of the foams, or by the addition of various additives.

The foams, including polyurethane, may be colored by adding dyes or pigment to the foams, during the foam preparation or in the post-treatment procedure. A variety of motifs can be printed on the polymeric foam tape substrates. Curing agents that are applied on the foam tape substrate can be dyed as well.

As non-limiting examples, the physical properties of the casting tapes and casting articles can be optimized for specific orthopedic application by altering the foam tape substrates properties, for example, chemical composition, density, elasticity, cell size and geometry, through addition of additives, preparation of blends, composites, etc. In addition, the tape casting and/or casting article properties can be optimized by altering the curing agents properties, such as, formulation, chemical composition, through addition of additives, lubricants, etc.

In some embodiments it might be preferred, that the polymeric foam tape substrates are hydrophobic, and in other embodiments it might be preferred that they are hydrophilic.

The polymeric foam tape substrate can be coated with various additives, polymers, or even foamed product to impart different properties, such as, various degrees of surface energy, hydrophobicity/hydrophilicity, rigidity, adhesion, etc.

Polymeric foam tape substrates used in the orthopedic tapes and casting articles of the present invention can be polyurethane foams. However, other types of cellular polymeric materials can be utilized as tape substrates (ex. polyolefin, polyester, etc.). The following examples are non-limiting. Polyurethane foams are in general prepared by the reaction of polyol and/or polyamine functionalized reactants with isocyanate-functionalized reactants. As non-limiting examples, polyols and/or polyamines can have the following chemical compositions: aliphatic, cycloaliphatic, aromatic, polyether, polyester, polycarbonate, hydrocarbone, silicone, acrylic, grafted polymers, or any combination thereof. As non-limiting examples, isocyanates can be aromatic, aliphatic and cycloaliphatic or their mixtures. Other non-limiting examples of suitable isocyanates include 2,4-toluene diisocyanate, 2,6-toluene diisocyanate, 2,4'-diphenylmethane diisocyanate, 4,4'-diphenylmethane diisocyanate, 4,4'-dicyclohexylmethane diisocyanate, etc. Mixtures of any isocyanates could be utilized as well. As non-limiting examples, water or low boiling solvents (e.g. pentane) can be used as a blowing agent in the preparation of the polymeric foams. Polyurethane foams can be made also by reacting blocked isocyanate and polyols or polyamines. In this reaction, a low boiling blocking agent is released and acts as a blowing agent. Polyurethane foams can also be made by introducing liquid or solid blowing agent to polyurethane thermoplastic resin. Polyurethane foams can be made with or without cell forming surfactants. In certain embodiments, polyurethane foams can be made with the presence of a cell forming surfactant. Various types of catalyst can, but do not necessarily have to be used in the polyurethane foam preparation. Examples of catalysts include urethane foaming catalyst dibutyltin dilaurate, blowing/gelling amine catalysts diazobicyclo octane, etc.

Polymeric foam tape substrates used in the present invention can be biodegradable. Polymeric foam tape substrates used in the present invention can contain flame retarding agents to make them non-flammable and/or self-extinguishing.

Synthetic casting tapes and casting articles can be prepared by coating or applying curable resins, and in some embodiments water curable resins, onto at least one polymeric foam tape substrate. It is preferred, but not necessary, to use water curable polyurethane (NCO-functional) prepolymer resins. Curable resins can be coated or applied onto polymer foam substrates according to any techniques utilized in coating of reactive (curable) resins on substrates (woven, knitted, non-woven, extruded, etc.), including, but not limited to, roller coating, spray coating, transfer coating, immersion coating, or any other method known to those in the art of coatings and coatings applications.

The application of the presented immobilization tapes and casting articles is in accordance to the methods in which synthetic casting tapes and other casting articles, that includes splints, are utilized.

The curable resin can be tacky or non-tacky, may contain some fillers, catalysts, isocyanate stabilizers, anti-foaming agents, etc. As a non-limiting example, it is noted that good absorption of the isocyanate reactive resin by the polyurethane foam tape substrate may reduce tackiness of the synthetic tapes that is often observed when other substrates are utilized. The composition and amount of resin applied onto the foam tape substrate can vary, and can be adjusted depending on the immobilization applications needs.

Polymeric foam tape substrates may, but do not necessarily have to, contain various fillers such as, but not limited to, barium sulfate, alumosilicate, calcium carbonate, fumed silica, which could increase the hardness and rigidity of the immobilization cast.

Polymeric foam tapes can be utilized as substrates for the Plaster of Paris as well. Partially or slightly hydrophilic foam tape substrate, or even foam tape substrate containing Plaster of Paris as a filler, can be used in Plaster of Paris casts.

The curable resin can be applied to one side of the polymeric foam tape substrate, both sides of the substrate, and/or it can be applied to the interior of the foam.

The immobilization tapes and casting articles of the present invention can be made of various lengths, thicknesses, and widths.

The immobilization tapes and casting articles of the present invention can be packaged in a way to minimize exposure to moisture, that includes dry packaging, vacuum packaging, and any procedures utilized in packaging of water curable synthetic casts and various other casting articles that include splints.

The following non-limiting examples, demonstrate immobilization tapes that utilize reticulated polyurethane foam tapes as substrates and isocyanate prepolymers as water curable resins.

EXAMPLES

Example 1

Reticulated polyether polyurethane foam of black color (Z/SIF, Product No. PDQZ45MA, FOAMEX International, Inc.) with about 45 pores per inch, density of about 2 pcf, extendibility of up to about 200%, and dimensions of about 12.0 inches by about 15.0 inches by about 2.25 inches. The foam was machine sliced into tape substrates with the following dimensions: about 12.0 inches by about 2.25 inches and thickness of about 1.0 mm (about 170 $cm^2$). The weight of this tape substrate was about 1.0 g.

Example 2

Reticulated polyether foam of beige color (Z/SIF1, Product No. EFLTZ88A, FOAMEX International, Inc.) with about 88 pores per inch, about 1.9 pcf density, extensibility of up to 200%, and dimensions of about 15.0 inches by about 10.0 inches by about 2.0 inches. It was sliced by machine cutting into tape substrates with the following dimensions: about 10.0 inches by about 2.0 inches and thickness of about 1.0 mm. The weight of this tape substrate was about 0.6 g.

Example 3

About 12.0 inches long and about 3.0 inches wide polyester substrate (about 228 $cm^2$), which are used in commercial synthetic casts, weighs about 4.9 g. The tape substrate of type from Example 1 (reticulated foam), with the approximately same area (about 228 $cm^2$) and nearly the same thickness (about 1 mm) as polyester substrate weigh significantly less, about 1.3 g.

Example 4

Commercially available (about 12 inches by about 3 inches) synthetic immobilization tape (Johnson & Johnson, Flash Cast Elite) with polyester substrate and NCO-prepolymer was dipped in water for about 5 seconds. The weight of the substrate was about 4.9 g and the weight of the water curable resin on the substrate about 5 g, for the total tape weight of about 9.9 g. The tape was applied, while slightly stretching, around a glass tube with the external diameter of about 25 mm that is coated with aluminum foil. The temperature of the tape increased during curing and it hardened (set) in about 5-6 minutes.

Example 5

NCO-prepolymer (of about 12% NCO content) was prepared by reacting polymeric isocyanate and short-chain diol. Tertiary amine catalyst (to promote curing with water) and defoaming agent were added to the resin. About 5.0 g of this resin were coated on the surface of the reticulated foam tape substrate, of type from Example 1 (about 12.0 inches by 2.25 inches by 1 mm), that by itself weighs about 1.1 g. The tape was dipped in water for about 5 seconds and then, while slightly stretching, was applied (wound) around a glass tube with the external diameter of about 25 mm that was coated with aluminum foil. The temperature of the tape increased slightly and hardened (set) in about 5 minutes.

Example 6

NCO-prepolymer (of about 12% NCO content) was prepared by reacting polymeric isocyanate and short-chain diol. Tertiary amine catalyst (to promote curing with water) and defoaming agent were added to the resin. About 7.5 g of the resin was coated to the reticulated foam tape substrate, of type from Example 1 (about 12.0 inches by about 2.25 inches by about 1 mm), that by itself weighs about 1.0 g. The tape was dipped in water for about 5 seconds and then was wound, while slightly stretching, around a glass tube with the external diameter of about 25 mm that was coated with aluminum foil. The tape hardened in about 5 minutes, and was harder than the cast in Example 5. Therefore, an increase in the amount of isocyanate resin in the casting tape can increase the hardness of the cured tape. Furthermore, addition of various fillers to foam tape substrates and changes in isocyanates water curable agent formulation can affect the physical properties of the cured tape.

Example 7

About 7.0 g of NCO-prepolymer (of 12% NCO content) resin containing tertiary amine catalyst and defoaming agent was coated onto reticulated foam tape substrate, of type from Example 1 (about 12.0 inches by about 2.25 inches by about 1 mm), which weigh about 0.7 g. The tape was transferred into a vacuum oven at room temperature in the moisture-free environment and kept for one hour to allow the resin to penetrate into the foam tape substrate. Afterwards, the tape was dipped in water for about 5 seconds and then was wound, while slightly stretching, around a glass tube with the external diameter of about 25.0 mm that was coated with aluminum foil. In this case, the tape before curing appeared less tacky than observed in previous Examples 4-6. Therefore, a method in which the curable resin is applied onto the tape substrate can affect the properties of the tapes before and after it has been cured. In certain embodiments related to manufacturing, the presence of water is minimized during the tape preparation.

Example 8

Polyurethane reticulated foam tape substrate, of type from Example 2, was coated with about 7.0 grams of NCO-prepolymer (of about 12% NCO content) resin containing tertiary amine catalyst and defoaming agent. The tape was dipped in water for about 5 seconds and then was wound, while slightly stretching, around a glass tube with the external diameter of about 25.0 mm that was coated with aluminum foil. This tape was significantly less tacky than observed in Examples 5-7. The tape hardened in about 3 minutes. Therefore, the absorption of curing agent into polymeric foam tape substrate can depend on the cell size and cell density of the foam tape substrate. In addition, the chemical make up of the foam tape substrate and curable resin can affect their compatibility and therefore absorption of the curable resin into the foam tape substrate. As a result properties of the tape before and after curing could be affected.

Example 9

Three casting samples (A, B, and C) were prepared similar to that in Example 8 utilizing the foam tape substrate from the foam of type from Example 2. In all cases the tackiness was lower than in Examples 4-7; the tapes were applied with standard gloves or even bare hands. It appears that most of the reactive resin was absorbed inside the tape substrate.

The compressive strength of the cured casts A, B, and C was measured by using an Instron Universal Tester. The compressive strength is given in Table 1.

TABLE 1

Compression properties of the casts

| | Cast # | | |
|---|---|---|---|
| | A | B | C |
| Tape substrate weight (g) | 0.60 | 0.72 | 0.55 |
| Prepolymer weight (g) | 5.0 | 5.0 | 5.0 |
| Total weight (g) | 4.94 | 5.47 | 5.13 |
| Inner/outer diameter of the cylindrical cast (mm) | 25/29.5 | 25/29.7 | 25/29.7 |
| Compression load at 2% strain (lbs) | 6.1 | 4.8 | 5.8 |
| Compression load at 5% strain (lbs) | 13.1 | 10.8 | 13.0 |
| Compression load at 10% strain (lbs) | 20.7 | 17.9 | 20.6 |
| Compression load at 20% strain (lbs) | 27.2 | 27.6 | 28.1 |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An article comprising a polymeric foam having a thickness of less than about 3/16 inch (about 5 mm) and one or more curable resins, wherein the polymeric foam substantially hardens upon curing.

2. The article of claim 1 wherein the polymeric foam is impregnated with the one or more curable resins.

3. The article of claim 1 wherein the polymeric foam is coated with the one or more curable resins.

4. The article of claim 1 wherein the continuous polymeric foam has a length greater than about one (1) inch.

5. The article of claim 1 wherein the polymeric foam is comprised of a thermoset or thermoplastic polymer.

6. The article of claim 1 wherein the polymeric foam has a substantially open cell structure, a substantially closed cell structure, or a substantially reticulated cell structure.

7. The article of claim 1 wherein the polymeric foam is flexible, semi-rigid, semi-flexible, viscoelastic, resilient or rigid.

8. The article of claim 1 wherein the polymeric foam has an average density of about 1.6 kg/m$^3$ to about 960 kg/m$^3$.

9. The article of claim 1 wherein the polymeric foam has a uniform or variable polymer composition structure.

10. The article of claim 1 wherein the polymeric foam has at least one variable property throughout, wherein the variable property is selected from the group consisting of density, cell density, cell geometry, cell size, affinity to water, elasticity, thickness and width.

11. The article of claim 1 further comprising a package for at least partially enclosing the polymeric foam.

12. The article of claim 11 wherein the package minimizes exposure to moisture.

13. The article of claim 1, wherein at least one of the one or more curable resins is cured via chemical reaction, UV light, laser light, radiation, or heat induced reaction.

14. An article comprising a cellular material and one or more curable resins, the cellular material having a thickness of less than about 3/16 inch (about 5 mm), wherein the cellular material substantially hardens upon curing.

15. An article comprising a polymeric foam having a thickness of less than about 3/16 inch (about 5 mm), one or more curable resins, and one or more additives, wherein the polymeric foam substantially hardens upon curing.

16. The article of claim 15 wherein the one or more additives is added to the polymeric foam.

17. The article of claim 15 wherein the one or more additives is added to the one or more curable resins.

18. The article of claim 15 wherein the one or more additives is capable of modifying the mechanical properties of the article.

19. The article of claim 15 wherein the one or more additives is capable of modifying the surface properties, tackiness and/or affinity to moisture of the article.

20. The article of claim 15 wherein the one or more additives is capable of modifying the reactivity properties of the article.

* * * * *